(12) United States Patent
Hirano et al.

(10) Patent No.: US 7,049,408 B2
(45) Date of Patent: May 23, 2006

(54) ANTIBODY REACTIVE WITH A PROTEIN HAVING PRE-B CELL GROWTH-SUPPORTING ABILITY

(75) Inventors: Toshio Hirano, 7-6, Anryu 2-chome, Suminoe-ku, Osaka-shi (JP) 559; Tsuneyasu Kaisho, Hyogo (JP)

(73) Assignee: Toshio Hirano, Osaka (JP)

( * ) Notice: Subject to any disclaimer, the term of this patent is extended or adjusted under 35 U.S.C. 154(b) by 0 days.

(21) Appl. No.: 09/828,217

(22) Filed: Apr. 9, 2001

(65) Prior Publication Data

US 2001/0051710 A1    Dec. 13, 2001

Related U.S. Application Data

(60) Continuation of application No. 09/182,563, filed on Oct. 29, 1998, now abandoned, which is a division of application No. 08/624,650, filed as application No. PCT/JP94/01732 on Oct. 14, 1994, now Pat. No. 5,914,252.

(30) Foreign Application Priority Data

Oct. 15, 1993  (JP)  .................................. 5-281622

(51) Int. Cl.
C07K 16/00   (2006.01)
C07K 16/28   (2006.01)
A61K 39/395  (2006.01)
C12N 5/20    (2006.01)

(52) U.S. Cl. ............... 530/387.1; 530/387.9; 530/388.1; 530/388.22; 530/389.1; 424/130.1; 424/141.1; 435/326; 435/346

(58) Field of Classification Search ............ 530/387.1, 530/387.9, 388.1, 388.22, 389.1
See application file for complete search history.

(56) References Cited

U.S. PATENT DOCUMENTS 5,914,252 A    6/1999  Hirano et al. ............... 435/69.5

FOREIGN PATENT DOCUMENTS

WO    WO98/35698    *    8/1998

OTHER PUBLICATIONS

Tsuneyasu Kaisho et al., "BST-1, A Surface Molecule of Bone Marrow Stromal Cell Lines That Facilitates Pre-B-Cell Growth", Proc. Natl. Acad. Sci, USA, vol. 91, pp. 5325-5329, Jun. 1994.

Tsuneyasu Kaisho et al., "Human Bone Marrow Stromal Cell Lines From Myeloma and Rheumatoid Arthritis That can Support Murine Pre-B-Cell Growth", The Journal of Immunology, vol. 149, No. 12, pp. 4088-4095, Dec. 15, 1992.

Brain C. Cunningham et al., "High-Resolution Epitope Mapping of hGH-Receptor Interactions by Alanine-Scanning Mutagenesis", Science, vol. 244, pp. 1081-1085.

David G. George et al., "Current Methods in Sequence Comparison and Analysis", Macromolecular Sequencing and Synthesis Selected Methods and Applications, Chapter 12, pp. 127-149, 1988.

Toshio Hirano et al., "Complementary DNA for a Novel Human Interleukin (BSF-2) That Induces B Lymphocyte to Produce Immunoglobulin", Nature, vol. 324, pp. 73-76, Nov. 6, 1986.

Jpn. J. Clin. Immuno., 15(6): 688-691, (1992) with attached English Translation.

Toshihiko Ohtomo, et al., "Molecular Cloning and Characterization of a Surface Antigen Preferentially Overexpressed on Multiple Myeloma Cells," Biochemical and Biophysical Research Communications, 258, 583-591 (1999).

Ed Harlow, "Antibodies a Laboratory Manual", Chapter 5, p. 7, Cold Spring Harbor Laboratory.

Jun Ishikawa et al., "Molecular Cloning and Chromosomal Mapping of a Bone Marrow Stromal Cell Surface Gene, BST2, That may be Involved in Pre-B-Cell Growth", Genomics, vol. 26, pp. 527-534, 1995.

T. Goto, et al., Blood, vol. 84, No. 6, pp. 1922-1930, "A Novel Membrane Antigen Selectively Expressed on Terminally Differentiated Human B Cells", Sep. 15, 1994.

S. Ozaki, et al., Blood, vol. 90, No. 8, pp. 3179-3186, "Immunotherapy of Multiple Myeloma With a Monoclonal Antibody Directed Against a Plasma Cell-Specific Antigen, HM1.24", Oct. 15, 1997.

K. Ono, et al., Molecular Immunology, vol. 36, pp. 387-395, "The Humanized Anti-HM1.24 Antibody Effectively Kills Multiple Myeloma Cells by Human Effector Cell-Mediated Cytotoxicity", 1999.

T. Goto, et al., Jpn. J. Clin. Hematol., vol. 32, pp. 1400, 1991.

(Continued)

*Primary Examiner*—Phillip Gambel
*Assistant Examiner*—Ilia Osuepsnki
(74) *Attorney, Agent, or Firm*—Oblon, Spivak, McClelland, Maier & Neustadt, P.C.

(57) ABSTRACT

A gene encoding a novel membrane protein polypeptide having pre-B cell growth-supporting ability and a membrane protein polypeptide consisting of 180 amino acid residues having pre-B cell growth-supporting ability. This gene encodes the membrane protein having pre-B cell growth-supporting ability. A method for producing a membrane protein having pre-B cell growth-supporting ability by transforming a host cell with a vector containing a gene encoding it and culturing the resulting transformants. A monoclonal antibody recognizing this membrane protein. The homogeneous and purified novel membrane protein pelypeptide can be produced in large quantities and used to produce monoclonal antibodies useful for identifying rheumatoid arthritis (RA) and for the preparation of reagents for the clinical diagnosis thereof.

7 Claims, 3 Drawing Sheets

OTHER PUBLICATIONS

K. Ozaki, et al., Tokushima J. exp. Med., vol. 43, pp. 7-15, "Localization and Imaging of Human Plasmacytoma Xenografts in Severe Combined Immunodeficiency Mice by a New Murine Monoclonal Antibody, Anti-HM1.24", 1996.

S. Ozaki, et al., Blood, vol. 93, No. 11, pp. 392-3930, "Humanized Anti-HM1.24 Antibody Mediates Myeloma Cell Cytotoxicity That is Enhanced by Cytokine Stimulation of Effector Cells", Jun. 1, 1999.

S. Ozaki, et al., Cancer, vol. 82, No. 11, pp. 2184-2190, "Radioimmunodetection of Human Myeloma Xenografts With a Monoclonal Antibody Directed Against a Plasma Cell Specific Antigen, HM1.24", Jun. 1, 1998.

* cited by examiner

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
       (A) LENGTH: 180 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 1:

```
Met Ala Ser Thr Ser Tyr Asp Tyr Cys Arg Val Pro Met Glu Asp Gly
1               5                   10                  15

Asp Lys Arg Cys Lys Leu Leu Gly Ile Gly Ile Leu Val Leu Leu
            20                  25                  30

Ile Ile Val Ile Leu Gly Val Pro Leu Ile Ile Phe Thr Ile Lys Ala
            35                  40                  45

Asn Ser Glu Ala Cys Arg Asp Gly Leu Arg Ala Val Met Glu Cys Arg
50                      55                  60

Asn Val Thr His Leu Leu Gln Gln Glu Leu Thr Glu Ala Gln Lys Gly
65                  70                  75                  80

Phe Gln Asp Val Glu Ala Gln Ala Ala Thr Cys Asn His Thr Val Met
                85                  90                  95

Ala Leu Met Ala Ser Leu Asp Ala Glu Lys Ala Gln Gly Gln Lys Lys
                100                 105                 110

Val Glu Glu Leu Glu Gly Glu Ile Thr Thr Leu Asn His Lys Leu Gln
                115                 120                 125

Asp Ala Ser Ala Glu Val Glu Arg Leu Arg Arg Glu Asn Gln Val Leu
            130                 135                 140

Ser Val Arg Ile Ala Asp Lys Lys Tyr Tyr Pro Ser Ser Gln Asp Ser
145                 150                 155                 160

Ser Ser Ala Ala Ala Pro Gln Leu Leu Ile Val Leu Leu Gly Leu Ser
                165                 170                 175

Ala Leu Leu Gln
            180
```

(2) INFORMATION FOR SEQ ID NO: 2:

(i) SEQUENCE CHARACTERISTICS:
       (A) LENGTH: 996 base pairs
       (B) TYPE: nucleic acid
       (C) STRANDEDNESS: double
       (D) TOPOLOGY: linear (ii) MOLECULE TYPE: cDNA to mRNA (xi) SEQUENCE DESCRIPTION: SEQ ID NO: 2:

```
GTGGAATTCA TGGCATCTAC TTCGTATGAC TATTGCAGAG TGCCCATGGA AGACGGGGAT    60

AAGCGCTGTA AGCTTCTGCT GGGGATAGGA ATTCTGGTGC TCCTGATCAT CGTGATTCT    120

GGGGTGCCCT TGATTATCTT CACCATCAAG GCCAACAGCG AGGCCTGCCG GGACGGCCT    180

CGGGCAGTGA TGGAGTGTCG CAATGTCACC CATCTCCTGC AACAAGAGCT GACCGAGGC    240

CAGAAGGGCT TTCAGGATGT GGAGGCCCAG GCCGCCACCT GCAACCACAC TGTGATGGC    300
```

```
CTAATGGCTT CCCTGGATGC AGAGAAGGCC CAAGGACAAA AGAAAGTGGA GGAGCTTGA        360

GGAGAGATCA CTACATTAAA CCATAAGCTT CAGGACGCGT CTGCAGAGGT GGAGCGACT        420

AGAAGAGAAA ACCAGGTCTT AAGCGTGAGA ATCGCGGACA AGAAGTACTA CCCCAGCTC        480

CAGGACTCCA GCTCCGCTGC GGCGCCCCAG CTGCTGATTG TGCTGCTGGG CCTCAGCGC        540

CTGCTGCAGT GAGATCCCAG GAAGCTGGCA CATCTTGGAA GGTCCGTCCT GCTCGGCTT        600

TCGCTTGAAC ATTCCCTTGA TCTCATCAGT TCTGAGCGGG TCATGGGCA ACACGGTTA         660

CGGGGAGAGC ACGGGGTAGC CGGAGAAGGG CCTCTGGAGC AGGTCTGGAG GGGCCATGG        720

GCAGTCCTGG GTGTGGGGAC ACAGTCGGGT TGACCCAGGG CTGTCTCCCT CCAGAGCCT        780

CCTCCGGACA ATGAGTCCCC CCTCTTGTCT CCCACCCTGA GATTGGGCAT GGGGTGCGG        840

GTGGGGGCA TGTGCTGCCT GTTGTTATGG GTTTTTTTG CGGGGGGGGT TGCTTTTTT          900

TGGGGTCTTT GAGCTCCAAA AAATAAACAC TTCCTTTGAG GGAGAGCAAA AAAAAAAA         960

AAAAAAAAA AAAAAAAAA AAAGAATTCC ACCACA                                   996
```

ANTIBODY REACTIVE WITH A PROTEIN HAVING PRE-B CELL GROWTH-SUPPORTING ABILITY

This application is a Continuation of U.S. application Ser. No. 09/182,563, filed Oct. 29, 1998, now abandoned, which is a Divisional application of U.S. application Ser. No. 08/624,650, filed May 22, 1996, now U.S. Pat. No. 5,914,252, issued Jun. 22, 1999, which is a 371 of PCT JP94/01732, filed Oct. 14, 1994.

TECHNICAL FIELD

The present invention relates to a gene and a novel membrane protein encoded by said gene, and more specifically, relates to a gene encoding a novel membrane protein polypeptide having pre-B cell growth-supporting ability, a vector containing said gene, transformants transformed by said vector and a method for producing the novel membrane protein polypeptide by using said gene.

The present invention further relates to a monoclonal antibody recognizing a novel membrane protein polypeptide having pre-B cell growth-supporting ability.

The gene of the present invention encodes a novel membrane protein polypeptide enhancing pre-B cell growth-supporting ability on the surface of synovial cells derived from patients with rheumatoid arthritis (RA). In the present invention, a homogeneous and purified novel membrane protein polypeptide having pre-B cell growth-supporting ability can be produced in large quantities by transforming appropriate host cells with a suitable vector in which the gene of the present invention is inserted. Thus, according to the present invention, it becomes possible to identify rheumatoid arthritis (RA), and also prepare reagents for the clinical diagnosis thereof.

BACKGROUND ART

Inflammatory cells in the synovial membrane and the synovial fluid of patients with rheumatoid arthritis (RA) are derived from peripheral blood and the migration of these cells to synovial membranes has not been explicated perfectly yet, but it is believed to be caused by a complicated interaction between chemical signals given to cells and protein (adhesion molecule) on cell membranes.

Various studies upon the significance of membrane proteins in arthritis have been performed. For example, it is known that an intercellular adhesion molecule-1 (hereinafter referred to as ICAM-1) is expressed on the inner layer of the synovial membrane and the blood vessel of the synovial membrane of patients with rheumatoid arthritis (RA), which is a ligand of a T cell surface molecule LFA-1 and causes both adhesion and migration of cells in the blood vessel wall [Hale et al.; Arthritis Rheum., 32:22 (1989), and Haynes et al.; Springer Semin. Immunopathol., 11:163 (1989)].

Similarly, it is suggested that a vasocellular adhesion molecule-1 (hereinafter referred to as VCAM-1,), which is a ligand of integrin VLA-4 expressed on T lymphoid cells (memory cells in particular) and monocytes, is expressed on the synovial membrane and fibroblast-like synovial cells of rheumatoid arthritis (RA) and osteoarthritis, [Morales-Ducret et al.; J. Immunol., 149:1424 (1992)], and further that a membrane protein called VAP-1 is expressed on the endothelial vein of a synovial membrane and may work as a specific recognition structure of leukocytes [Salmi et al.; Science, 257, 1407 (1992)].

The present inventors have engaged in extensive studies with a view to investigating the function of the bone marrow microenvironments in disorders causing abnormalities of B cells, and have found that the pre-B cell growth-supporting ability of bone marrow stromal cells derived from patients with rheumatoid arthritis (RA) and multiple myeloma (MM) is enhanced in comparison with that of healthy donor-derived bone marrow stromal cells and that the direct contact of pre-B cells with stromal cells might play an essential role in this supporting ability. And the present inventors have established novel stromal cell lines (RASV5-5, MMSV3-3) containing a molecule enhancing the growth of pre-B cells by cell-lining stromal cells of patients, and have found that the pre-B cell growth-supporting activity of these stromal cell lines is most likely caused by unknown adhesion molecules different from known stem cell factors (SCF), ICAM, CD44, VCAM-1, LFA-1α, LFA-1β, NCAM and FLAM-1 [J. Immunol., 149:4088 (1992)].

Further, since it has been suggested that the synovial cell line SynSV6-14 established from the synovial cell derived from patients with rheumatoid arthritis (RA) has pre-B cell growth-supporting ability similarly to the stromal cell line RASV5-5 derived from the bone marrow of patients with rheumatoid arthritis (RA), the present inventors have obtained a novel monoclonal antibody which responds to these cell lines but does not respond to the stromal cell line NFSV1-1 derived from the human bone marrow having no pre-B cell growth-supporting ability, and at the same time have succeeded in cloning genes encoding its antigen membrane protein (Bst-1) (Japanese Patent Application No. 5-141178/1993).

DISCLOSURE OF INVENTION

The present inventors have obtained a novel mouse monoclonal antibody RS38 which responds to SynSV6-14 but does not respond to the healthy bone marrow stromal cell line NFSV1-1 and recognizes a membrane protein different from the above Bst-1 at the process of producing various mouse monoclonal antibodies recognizing a membrane protein expressed on the synovial cell derived from patients with rheumatoid arthritis (RA) but not expressed on the cell derived from healthy donors. Subsequently, the present inventors have succeeded in isolating clones encoding a novel membrane protein responding to said RS38, accroding to screening a cDNA library prepared from a synovial cell line derived from patients with rheumatoid arthritis (RA) by using the RS38 antibody, which has led to the completion of the present invention.

That is, the present invention is directed to provide a novel membrane protein polypeptide having pre-B cell growth-supporting ability, a gene encoding said polypeptide, a vector containing said gene, transformants transformed by said vector and a method for producing a novel membrane protein by using said gene.

Further, the present invention is directed to provide a monoclonal antibody recognizing a novel membrane protein having pre-B cell growth-supporting ability.

The present invention for accomplishing the above object consists of the following (1)–(7).

(1) A novel membrane protein polypeptide containing an amino acid sequence shown in sequence No. 1 of the sequence table or a part of the amino acid sequence and being expressed on the synovial membrane of patients with rheumatoid arthritis.

(2) A DNA encoding a polypeptide containing an amino acid sequence shown in sequence No. 1 of the sequence table or a part of the amino acid sequence.
(3) The DNA according to the above (2), characterized by containing a base sequence which hybridizes the base sequence shown in sequence No. 2 of the sequence table or a base sequence derived from said base sequence having at least one amino acid residue substituted, removed or added partially.
(4) A recombinant vector containing the DNA according to the above (2) or (3).
(5) A prokaryotic or eukaryotic host cell, characterized by being transformed with the recombinant vector according to the above (4).
(6) A method for producing the polypeptide containing an amino acid sequence shown in sequence No. 1 of the sequence table or a part of the amino acid sequence, characterized by culturing the host cell according to the above (5).
(7) A monoclonal antibody recognizing a polypeptide containing an amino acid sequence shown in sequence No. 1 of the sequence table or a part of the amino acid sequence.

Subsequently, the present invention will be described in detail.

The monoclonal antibody of the present invention may be prepared in the following manner essentially.

That is, the antibody of the present invention may be prepared by using a synovial cell derived from patients with rheumatoid arthritis (RA) having pre-B cell growth-supporting ability as an antigen, immunizing it according to an ordinary immunization method, cell-fusing the immunized cell according to an ordinary cell fusion method and cloning the fused cell according to an ordinary cloning method.

More specifically, as a preferable method for producing the monoclonal antibody of the present invention may be exemplified a method comprising using the cell line SynSV6-14, derived from the synovial membrane of patients with rheumatoid arthritis (RA) and established as a culture cell, as the above-mentioned antigen, fusing the plasma cell (immunocyte) of a mammal immunized with said antigen with a myeloma cell of a mammal such as a mouse, cloning the obtained fused cell (hybridoma), selecting clones producing the antibody of the present invention recognizing SynSV6-14 of them, and culturing them to recover the objective antibody.

In the method for producing the above monoclonal antibody, mammals to be immunized with the antigen are not particularly restricted; it is preferable to select one taking compatibility with a myeloma cell to be used for cell fusion into consideration and generally, a mouse, a rat and a hamster are used.

Immunization is performed according to a general method, for example, by administering cultured cells of the cell line SynSV6-14 derived from the synovial membrane of patients with rheumatoid arthritis (RA) into the peritoneal cavity of a mammal according to injection. More specifically, it is preferable to dilute it with or suspend it in PBS or physiological saline to a proper amount and administer it into an animal several times every 4–21 days, together with an ordinary adjuvant if required. In addition, an ordinary carrier (Schlepper) may be employed on the above administration. As an immunocyte, a splenic cell obtained after the final administration of the above cell line is used preferably.

As a myeloma cell of a mammal as the other parent cell to be fused with the above immunocyte may be preferably used known various cell lines including P3 (P3X63Ag8.653) [J. Immunol., 123:1548 (1978)], p3-U1 [Current Topics in Micro-biology and Immunology, 81:1–7 (1978)], NS-1 [Eur. J. Immumol., 6:511–519 (1976)], MPC-11 [Cell, 8:405–415 (1976)], SP2/0 [Nature, 276: 269–270 (1978)], FO [J. Immunol. Meth., 35:1–21 (1980) ], S194 [J. Exp. Med., 148:313–323 (1978)] and R210 [Nature, 277:131–133 (1979)].

The cell fusion of the above immunocyte with a myeloma cell may be performed essentially according to a known method, for example, a method by Milstein et al. [Methods Enzymol., 73:3–46 (1981)].

More specifically, the above cell fusion may be performed, for example, in an ordinary nutrition medium in the presence of a fusion-accelerating agent. Examples of the fusion-accelerating agent include polyethylene glycol (PEG) and Sendai virus (HVJ), and moreover, auxiliary agents such as dimethyl sulfoxide may be added properly if required in order to enhance the fusing effect. Regarding the ratios of immunocytes and myeloma cells used, the former is preferably used in an amount 1–10 times that of the latter. Examples of a medium used in the above cell fusion include an RPMI-1640 medium and an MEM medium suitable for the proliferation of the above myeloma cell line and other mediums ordinarily used for the culture of this kind of cell, and in addition, supplementary serum such as fetal calf serum (FCS) may be used together.

Cell fusion is performed by mixing prescribed amounts of the above immunocytes and myeloma cells thoroughly in the above medium, adding a PEG solution preheated to about 37° C., for example, PEG with an average molecular weight of the order of 1,000–6,000, to the medium ordinarily at a concentration of about 30–60% (W/V) and mixing them. Subsequently, by repeating the operations of adding proper mediums to them successively and centrifuging the reaction mixture, and removing the supernatants can be formed an objective hybridoma.

Said hybridoma is selected by culturing in an ordinary selective medium, for example, an HAT medium (medium containing hypoxanthine, aminopterin and thymidine). The culture in said HAT medium is continued for a time sufficient for cells other than objective hybridomas (non-fused cells) to die out, ordinarily for several days to several weeks. Subsequently, the screening and monocloning of the hybridomas producing the objective antibody are performed according to an ordinary limiting dilution analysis.

The thus prepared hybridomas producing the monoclonal antibody of the present invention may be subcultured in an ordinary medium and stored in liquid nitrogen for a long time.

In order to collect the monoclonal antibody of the present invention from said hybridomas may be employed a method comprising culturing said hybridomas according to an ordinary method and obtaining it from the supernatants or a method comprising administering a hybridoma into a appropriate mammal to proliferate and obtaining it from its ascites. The former is suitable for obtaining an antibody with a high purity and the latter is suitable for the mass production of the antibody.

Moreover, the antibody obtained according to the above method may be purified to have a high purity employing an ordinary purification means such as a salting out technique, gel filtration and affinity chromatography.

The thus prepared monoclonal antibody of the present invention makes it possible to identify synovial cells of patients with rheumatoid arthritis (RA) expressing a novel membrane protein of an antigen with a high sensitivity and a high precision according to an ordinary immunological means such as radioimmunoassay (RIA), enzyme immunoassay (EIA) and immunofluorescence analysis.

The gene of the present invention is obtained by preparing mRNA from a synovial cell of patients with rheumatoid arthritis (RA) expressing a membrane protein having human pre-B cell growth-supporting ability, and then converting it into a double-stranded cDNA according to a known method. As a cell used for preparing the mRNA can be mentioned, for example, a cell line SynSV6-14 used as an immune source of a hybridoma RS38, but it is not limited to the cell line and therefore any type of cells expressing the membrane protein having human pre-B cell growth-supporting ability may be used. Incidentally, SynSV6-8 was used in the present invention.

For the preparation of the total RNA for obtaining mRNA can be employed a method for obtaining the total RNA which consists of performing cesium chloride density-gradient centrifugation after a guanidine thiocyanate treatment [Chirgwin et al., Biochemistry, 18:5294 (1979)], a method which consists of performing a surfactant treatment and a phenol treatment in the presence of the ribonuclease inhibitor of a vanadium complex [Berger & Birkenmeier, Biochemistry, 18:5143 (1979)], and other known methods.

The preparation of mRNA from the total RNA can be accomplished by recovering poly(A)$^+$RNA from the total RNA according to, for example, affinity column chromatography using an oligo (dT)-bound carrier, for example, cephalose or cellulose, or a batch method. Besides, poly(A)$^+$RNA can be further purified according to sucrose density-gradient centrifugation. In addition, there can be mentioned a method for obtaining poly(A)$^+$RNA directly without preparing RNA or a convenient method using a commercially available kit.

In order to obtain a double-stranded cDNA from the thus obtained mRNA, for example, a DNA (cDNA) complementary to mRNA is synthesized by using mRNA as a template, and using an oligo (dT) complementary to a poly-A-chain sited at the 3' end as a primer, and then treating it with reverse transcriptase.

The double-stranded cDNA can be also obtained by degrading mRNA according to an alkaline treatment, subjecting the obtained single-stranded cDNA as a template to a treatment with reverse transcriptase or DNA polymerase (e.g., Klenow fragment), and then treating it with SI nuclease, or treating it directly with RNase and DNA polymerase [Maniatis et al., Molecular Cloning, Cold Spring Harbor Laboratory (1982) and Gubler & Hoffman, Gene, 25:263 (1983)]. Nowadays, convenient kits have been on the market, and a double-stranded cDNA can be obtained by using them.

The cDNA library can be obtained by inserting the thus obtained cDNA into a proper vector, for example, an EK-type plasmid vector such as pBR322 and pSC101, and a phage vector such as λ gt10, and then transforming *Escherichia coli* with said vector (e.g., X1776, HB101, DH1, DH5) or the like (refer, for example, to "Molecular Cloning" above).

On the other hand, host cells of other prokaryotes and eukaryotes can be transformed by using a suitable expression vector in which the double-stranded cDNA obtained according to the above-mentioned method is inserted.

The ligation of the double-stranded cDNA to the vector can be performed by adding a proper chemically-synthesized DNA adapter thereto, and subjecting it with a vector DNA cleaved by means of a restriction enzyme in advance to a treatment with T4 phage DNA ligase in the presence of ATP.

The expression vector of the present invention contains a replicative origin, a selective marker, a promoter located in the upstream region of a gene to be expressed, an RNA splice site and a polyadenylated signal.

As a gene expression promoter in a mammal cell may be used virus promoters such as retrovirus, polyoma virus, adenovirus and simian virus (SV) 40, and promoters derived from cells such as human polypeptide chain elongation factor 1α (HEF-1α). For example, in case of using a promoter of SV40, it can be performed easily according to a method of Mulligan et al. [Nature, 277:108 (1979)].

As a replicative origin can be used those derived from SV40 polyoma virus, adenovirus and bovine papilloma virus (BPV), and as a selective marker can be used a phosphotransferase APH (3') II or I (neo) gene, a thymidine kinase (TK) gene, an *Escherichia coli* xanthine-guanine phosphoribosyl transferase (Ecogpt) gene and a dihydrofolate reductase (DHFR) gene.

In order to express the desired gene using a prokaryotic cell as a host cell, the host cell is transformed with a replicon derived from species capable of being fitted for hosts, namely, a plasmid vector containing a replicative origin and a regulation sequence. A vector which has a marker gene capable of imparting the selectivity of a phenotype to transformed cells is preferable. For example, in case of using *Escherichia coli* as a host cell, it can be transformed using pBR322, a vector originated from the host cell [Boliver et al., Gene, 2:95 (1975)]. The pBR322 contains an ampicillin resistant gene and a tetracycline resistant gene, and therefore transformants can be identified by utilizing either of these resistant properties.

As a promoter needed for the gene expression of a prokaryotic host cell can be mentioned a promoter of a β-lactamase gene [Chang et al., Nature, 275:615 (1978) ], a lactose promoter [Goeddle et al., Nature, 281:544 (1979)], a tryptophan promoter [Goeddle et al., Nucleic Acid Res., 8:4057 (1980)], a tac promoter and the like preferably; however, it is not limited to them.

As a prokaryotic host cell of hosts to be used in the expression system of the present invention can be mentioned *Escherichia coli, Basillus subtilis, Bacillus thermophilus* and the like preferably; however, it is not limited to them.

In addition, as an eukaryotic host cell can be mentioned eukaryotic microorganisms such as *Saccharomyces cerevisiae*, and cells derived from mammals such as a COS cell, a Chinese hamster ovary (CHO) cell, a C127 cell, a 3T3 cell, a Hela cell, a BHK cell, a namalwa cell and a human fetal renal cell (293 cell) preferably; however, it is not limited to them.

Incidentally, the culture of the transformants of the present invention may be performed by selecting culture conditions suitable for host cells appropriately.

The isolation of a cDNA encoding a membrane protein having pre-B cell growth-supporting ability of the present invention can be performed, for example, by using pre-B cell growth-supporting ability as an index or according to a method such as direct expression cloning using an antibody.

The measurement of pre-B cell growth-supporting ability can be performed by using a murine pre-B cell line DW34 [Eur. J. Immunol., 18:1767 (1988)]. That is, a cell expressing the membrane protein having pre-B growth-supporting ability is cultured until it becomes subconfluent on 24-well plates (preferable density being about 50%) and a proper amount of radiation is irradiated thereupon, DW34 of 1 to $2 \times 10^3$ per well is added thereto, and cultured in the RPMI-1640 medium containing 10% FCS under the condition of 5% $CO_2$ at 37° C. for about 4 to 6 days. The degree of the enhancement of the growth-supporting ability can be found by examining the number of viable cells of DW34 in each well according to trypan blue dye exclusion.

In the present invention, the desired gene could be cloned by repeating the steps, which consist of selecting a transformant expressing a membrane protein according to flow cytometry by means of an FACScan using a monoclonal antibody RS38 recognizing the novel membrane protein on the synovial cell of patients with rheumatoid arthritis (RA), preparing a transformant again by sorting the plasmid DNA used for the preparation of the transformant, and then screening the transformant according to flow cytometry.

Specifically, a transduced transformant (293T cell) was cultured on well plates and removed from the plates with PBS containing 0.02% EDTA, and after the cell was washed with an FACS buffer solution composed of PBS containing 2% FCS and 0.02% $NaN_3$, it was reacted with RS38 as a primary antibody. Subsequently, after the unreacted primary antibody was removed by washing it with an FACS buffer solution, it was further reacted with a secondary antibody, an FITC-labeled antibody (FITC-labeled anti-mouse goat Ig antibody), dead cells were stained with propidium iodide, and viable cells were analyzed by an FACScan to select transformants responding strongly to RS38.

Further, the complete length of cDNA (pRS38-BOS) encoding a membrane protein polypeptide having novel pre-B cell growth-supporting ability shown in sequence No. 2 of the sequence table could be obtained by repeating the steps, which consist of treating *Escherichia coli* (DH5) containing the cDNA used for the preparation of transformants responding to the antibody with alkali to select a group of plasmids containing the desired gene, subdividing the group of plasmids into some groups of plasmids, transducing them into 293T cells again, and then selecting transformants according to FACScan analysis using the above-mentioned monoclonal antibody RS38.

Incidentally, the *Escherichia coli* DH5α strain containing pRS38-pUC19 with the cDNA inserted into the XbaI cleavage sites of a pUC19 vector was deposited at National Institute of Bioscience & Human Technology, Agency of Industrial Science and Technology in Japan, which is an international depositary authority according to Budapest Treaty on the international recognition of the deposit of microorganisms for the purpose of patent procedure, on Oct. 5, 1993, under the name of *Escherichia Coli* DH5α (pRS38-pUC19) with accession No. FERM BP-4434.

Generally, the genes of eukaryotes are thought to show polymorphism as known according to human interferon genes [e.g., Nishi et al., J. Biochem., 97: 153 (1985)], and in some cases at least one amino acid is substituted according to this polymorphism, and in other cases amino acids do not change at all though there are changes in the DNA sequence.

Further, it is probable that some polypeptides having at least one more or less amino acid than the amino acid sequence shown in sequence No. 1 of the sequence table, or some polypeptides substituted with at least one amino acid may also have the same function as that of the novel membrane protein of the present invention (pre-B cell growth-supporting ability). Actually, for example, it has been already known that the polypeptide obtained from a human interleukin-2 (IL-2) gene, in which a DNA sequence corresponding to cysteine is converted to a sequence corresponding to serine, also holds an IL-2 activity [wang et al., Science, 224:1431 (1984)].

Moreover, a known protein gene and a gene shown in sequence No. 2 of the sequence table can be ligated by means of a proper restriction enzyme or adapter to yield a polypeptide bound to the known protein. As the known protein gene can be mentioned immunoglobulin, and it may be bound to a Fc portion thereof using the gene shown in sequence No. 2 of the sequence table instead of the variable region site thereof [(Zettlmeissl et al., DNA AND CELL BIOLOGY, 9:347–353 (1990)].

Furthermore, in case of expressing a polypeptide in eukaryotic cells, glycosylation occurs in many cases, and the glycosylation can be regulated according to the conversion of at least one amino acid; in this case, too, it may have the same function as that of the novel membrane protein polypeptide of the present invention. Therefore, even the genes in which the site encoding the membrane protein polypeptide of the present invention are modified artificially according to various methods as above and polypeptides can be included in the present invention so far as the polypeptides obtained from the genes have the same function as that of the membrane protein polypeptide of the present invention.

Moreover, it goes without saying that genes to be hybridized with genes shown in sequence No. 2 of the sequence table and polypeptides are also included in the present invention so far as the polypeptides expressed from the genes have the same function as that of the membrane protein polypeptide of the present invention (pre-B cell growth-supporting ability). In this case, hybridization may be carried out according to employing ordinary hybridization conditions (for example, refer to the above-mentioned "Molecular Cloning").

The desired homogeneous and purified soluble membrane protein polypeptide having pre-B cell growth-supporting ability can be obtained by culturing a transformant transformed with a gene encoding the polypeptide, solubilizing the yielded polypeptide with a proper detergent, subjecting the resultant polypeptide to separation and purification. Preferable examples of the detergent include Nonidet P-40 (NP-40), Sodium Dodecyl Sulphate (SDS), Triton X-100, Tween 20 and the like.

Figure 3:
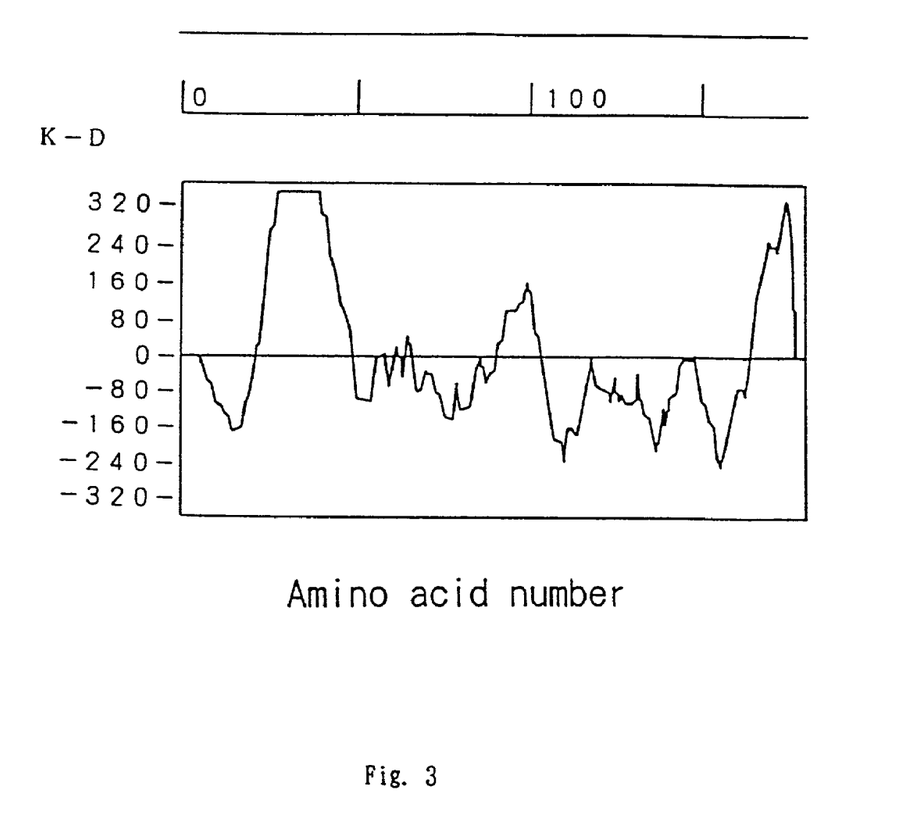
FIG. 3 shows the results of analyzing the hydrophobic region and the hydrophilic region of a gene obtained in Examples of the present invention by means of a DNA analysis software Gene Works.

In addition, soluble membrane proteins can be also prepared according to gene engineering. Namely, as shown in FIG. 3, since RS38 is guessed to be a cell membrane through-type protein having a cell membrane through domain and an intracellular domain at the side of the N terminal, soluble RS38 with the 49th Asn of sequence No. 1 of the sequence table as the N end can be prepared by employing a PCR-mutagenesis method [M. Kamman et al., Nucl. Acids Res., 15:5404 (1989)]. In this case, as a signal sequence may be used known ones and examples thereof include the signal sequence of Bst-1 (Japanese Patent Application No. 5-141178/1993) and that of G-CSF (Japanese Patent Publication No. 2-5395/1990).

As a means of separation and purification of the membrane protein polypeptide, a method to be used in the case of ordinary protein can be employed; for example, the membrane protein polypeptide of the present invention can be separated and purified properly by selecting and combining various types of chromatograpy such as affinity chromatography using the above-mentioned monoclonal antibody, ultrafiltration, salting out, dialysis and the like.

The present invention will be described in detail according to Referential Examples and Examples hereinafter, although the present invention is not limited to these Examples.

REFERENTIAL EXAMPLE 1

Establishment of a Stromal Cell Line Derived from Healthy Donors

Stromal cells derived from healthy donors were electroporated with a pAct-SVT plasmid containing an SV40 large T antigen cDNA and a chick β-actin promoter [BBRC, 186:129–134 (1992)] by means of a Gene Pulser (manufactured by BioLad). Namely, 0.8 ml of an aliqout of the stromal cells of $1 \times 10^7$ cells/ml derived from healthy donors in PBS were mixed with 10 μg of the plasmid, and the mixture was incubated on ice for 10 minutes, subjected to electroporation under the conditions of 250 V and at an electrostatic capacity of 250 μF, further incubated on ice for 10 minutes, suspended in the RPMI-1640 medium (manufactured by GIBCO) containing 10% FCS (manufactured by Bioproducts), and cultured in a 10-centimeter culture dish. The culture medium was changed every three days, and colonies of well-grown adhesive cells were harvested about 2 weeks later with a small piece of filter paper impregnated with trypsin to obtain a stromal cell line (NFSV1-1) derived from the bone marrow of healthy donors [J. Immunol., 149:4088 (1992)].

REFERENTIAL EXAMPLE 2

Establishment of Synovial Cell Lines Derived from Patients with Rheumatoid Arthritis (RA)

Synovial cells derived from patients with rheumatoid arthritis (RA) were electroporated with a pAct-SVT plasmid containing an SV40 large T antigen cDNA and a chick β-actin promoter [BBRC, 186:129–134 (1992)] by means of a Gene Pulser (manufactured by BioLad). Namely, 0.8 ml of an aliqout of the synovial cells of $1 \times 10^7$ cells/ml derived from patients with RA in PBS were mixed with 10 μg of the plasmid, and the mixture was incubated on ice for 10 minutes, subjected to electroporation under the conditions of 250 V and at an electrostatic capacity of 250 μF, further incubated on ice for 10 minutes, suspended in the RPMI-1640 medium (manufactured by GIBCO) containing 10% FCS (manufactured by Bioproducts), and cultured in a 10-centimeter culture dish. The culture medium was changed every three days, and colonies of well-grown adhesive cells were harvested about 2 weeks later with a small piece of filter paper impregnated with trypsin to obtain synovial cell lines (SynSV6-8 and SynSV6-14) derived from patients with rheumatoid arthritis (RA).

BEST MODE FOR CARRYING OUT THE INVENTION

The embodiment of the present invention will be described in detail hereinafter.

EXAMPLE 1

Preparation of Monoclonal Antibodies

1) Antigen and Immunization

The synovial cell line SynSV6-14 derived from patients with rheumatoid arthritis (RA) having pre-B cell growth-supporting ability obtained in the above Referential Example 2 was used as an antigen for immunization. Using the RPMI-1640 medium (manufactured by GIBCO) containing 10% fetal calf serum (FCS, manufactured by Bioproducts) and 50 μM 2-mercaptoethanol as a medium, the cell line was subcultured in an incubator containing 5% $CO_2$, at 37° C.

The cells were treated with 0.02% EDTA and PBS, and recovered from a culture flask of the incubator according to pipetting. The cells were suspended into the RPMI medium at a rate of about $1 \times 10^7$ cells/ml, and immunized to a BALB/C mouse (4-week old, female, manufactured by S. L. C. of Japan). In the initial immunization, about $1 \times 10^7$/ml cells were injected into the peritoneal cavity of the mouse, and 2 to 3 weeks later, $1 \times 10^7$/ml cells were injected as additional immunization. Further, at intervals of 2 to 3 weeks, $1 \times 10^7$/ml cells were injected 2 to 3 times as additional immunization, and 3 days after the final immunization, the mouse was sacrificed and the spleen was obtained for fusion.

2) Cell Fusion

After the spleen extirpated from one mouse was cut to pieces, isolated spleen cells were centrifuged, suspended into RPMI-1640 medium (manufactured by GIBCO) and washed sufficiently. On the other hand, $1 \times 10^7$ cells obtained by culturing a mouse-myeloma cell line P3X63Ag8.653 [J. Immunol., 123:1548 (1979)] in the DMEM medium (manufactured by GIBCO) containing 10% fetal calf serum (FCS, manufactured by FILTRON) were washed in the above DMEM medium similarly, and were introduced into a centrifugal tube together with $1 \times 10^8$ of said spleen cells and mixed, and then were subjected to cell-fusion with polyethylene glycol 1500 (manufactured by Boehringer) according to ordinary procedure [Clin. Exp. Immunol., 42:458–462 (1980)].

The obtained fused cells were introduced into 96-well plates in the DMEM medium containing 10% FCS, and cultured in an incubator containing 5% $CO_2$, at 37° C. From the following day, the medium was replaced with the HAT selective medium (complete RPMI-1640 medium containing $1.0 \times 10^{-4}$ M hypoxanthine, $4.0 \times 10^{-7}$ M aminopterin and $1.6 \times 10^{-5}$ M thymidine having 10% FCS and 50 μM 2-mercaptoethanol added thereto) slowly, and the culture was continued. After the culture was initiated, half of the supernatant was replaced with a new HAT medium 2 times per week, and the culture was continued to maintain proliferation.

The thus obtained fused cells were cloned according to limiting dilution analysis.

That is, using the antibodies in the culture supernatant obtained by culturing the above fused cells, respondency with the antigen was examined, and clones having strong respondency with the antigen alone were obtained according to ordinary procedure employing limiting dilution analysis.

So as to perform the formation of clones, the above hybridoma and the spleen cells of a BALB/C mouse were prepared in prescribed amounts, inoculated onto 96-well plates at a rate of 1 to 10 hybridoma(s) per well, and cultured in an incubator containing 5% $CO_2$, at 37° C. The operation of cloning hybridomas grown was repeated in the same manner according to ordinary limiting dilution analysis until they became a single clone theoretically. Clones yielding the desired antibody were screened using the above antigen.

3) Screening

The screening of fused cells (hybridomas) was performed according to indirect fluorescent antibody technique, flow cytometry analysis by means of a flow cytometer.

The screening of clones yielding the objective antibody was performed using a) SynSV6-14 (antigen for immunization) and b) the bone marrow stromal cell line NFSV1-1 derived from healthy donors as target cells. Namely, after immunizing the synovial cell line (SynSV6-14) derived from patients with rheumatoid arthritis (RA) having pre-B cell growth-supporting ability to a BALB/C mouse, the screening of monoclonal antibodies responding to SynSV6-14 but not responding to the bone marrow stromal cell line (NFSV1-1) derived from healthy donors having no pre-B cell growth-supporting ability was performed as follows. The first screening was performed using SynSV6-14, a cell to be subjected to reaction, as an antigen for immunization. First of all, culture supernatants responding to SynSV6-14 were selected with a view to selecting fused cell clones responding to said SynSV6-14, and then a primary screening was performed.

Namely, cells suspended in a reaction buffer (PBS containing 2% FCS and 0.02% NaN$_3$) were suspended into 20 µl of a hybridoma culture supernatant (about 5×10$^5$/20 µl), and reacted at 4° C. for 20 minutes.

They were washed with the above buffer twice, and the FITC-labeled anti-mouse Ig goat antibody (manufactured by Cappel) was added thereto, and the mixture was incubated for 20 minutes. After the reaction product was washed three times, it was analyzed by means of a flow cytometer (FACScan, manufactured by Becton Dickinson).

Subsequently, the bone marrow stromal cell line NFSV1-1 derived from healthy donors was used as a cell to be subjected to reaction and analyzed by means of a flow cytometer as above. A hybridoma yielding antibodies responding more strongly to SynSV6-14 was obtained according to it.

Thus, a hybridoma (RS38) yielding antibodies responding to SynSV6-14 but not responding to the bone marrow stromal cell line NFSV1-1 derived from healthy donors was isolated. The antibodies yielded by the hybridoma were IgM, κ-type.

Incidentally, the hybridoma yielding the above monoclonal antibody RS38 is a novel fused cell prepared from a BALB/C mouse spleen cell and mouse-myeloma P3X63Ag8.653 as parent cells and was deposited at National Institute of Bioscience & Human Technology, Agency of Industrial Science and Technology, AIST Tsukuba Central 6,1-1, Higashi 1-chome, Tsukuba-shi, Ibaraki-Ken 305-8566, Japan which is an international depositary authority according to Budapest Treaty on the international recognition of the deposit of microorganisms for the purpose of patent procedure, on Oct. 5, 1993, under the name of Mouse-Mouse hybridoma RS38 with accession No. of FERM BP-4433.

4) Purification of Antibodies

The fused cells prepared in the above 2) were cultured according to ordinary procedure, and the antibodies yielded in the culture supernatant were purified according to ordinary procedure.

That is, hybridomas were collected from the wells with the highest antibody titer to the above antigen, and one well in which the growth of cells could be recognized was taken out, and the obtained culture cells were expanded into a tissue culture flask under the conditions of 5% CO$_2$ at 37° C. and were grown. The obtained cells were injected into the peritoneal cavity of a BALB/C mouse (6-week old, female, manufactured by S. L. C. of Japan) with pristan dosed. And 10 to 14 days after, the ascites was collected, salted out with 50% ammonium sulfate, dialyzed with PBS and purified with a QAE column. The antibodies were further salted out and dialyzed sufficiently to obtain a purified product of about 6 mg/ml.

EXAMPLE 2

Properties of the Monoclonal Antibodies

1) Distribution of Cell Lines

The distribution of the RS38 antigen in various cell lines (various cell lines shown in Table 1) was analyzed by means of an FACScan. That is, each of various cell lines was suspended in an FACS buffer solution comprising PBS containing 2% FCS and 0.02% NaN$_3$, in the presence of 10 µg/ml of the mouse monoclonal antibody RS38 obtained as a primary antibody in Example 1, and incubated on ice for 20 minutes. After washed with an FACS buffer solution twice, the resultant product was further incubated on ice for 15 minutes using an FITC-labeled anti-mouse Ig goat antibody (manufactured by Cappel) as a secondary antibody. Propidium iodide (PI) was added therein so that the final concentration of it became 1 µ/ml, and the mixture was further incubated on ice for 5 minutes. After the resultant product was washed with the FACS buffer solution three times, the cells were analyzed with light scattering measurement and viable cells alone were subjected to analysis by means of an FACScan (manufactured by Becton Dickinson). As controls were used mouse monoclonal antibodies SG2 and RF3 (Japanese Patent Application No. 5-141178/1993). The results are shown in Table 1. As is apparent from Table 1, it was revealed that the distribution of the RS38 is different from that of SG2 and RF3.

TABLE 1

Results of FACS analysis on Cell Lines

| Origen | Cell Line | SG2/RF3 | RS38 |
|---|---|---|---|
| T cell line | MOLT-4 | − | +/− |
|  | JURKAT | + | − |
| B cell line | Raji | − | − |
|  | Paudi | − | − |
|  | CL4 | − | ++ |
|  | Ramos | − | − |
| Myeloid | U937 | + | + |
|  | K562 | − | + |
|  | HL60 | − | +/− |
|  | M07 | − | + |
| Miscellaneous | HepG2 | − | +/− |
|  | T24 | − | +/− |
|  | SKWG-4(P122) | − | +/− |
|  | Hela | − | +/− |

EXAMPLE 3

1. Preparation of a cDNA Library

1) Preparation of Poly (A)$^+$RNA

The preparation of poly (A)$^+$RNA from the synovial cell line SynSV6-8 derived from patients with rheumatoid arthritis (RA) was performed using a Fast Track™ mRNA isolation kit version 3.2 (manufactured by Invitrogen). That is, SynSV6-8 cells for twenty 10-centimeter culture dishes were homogenized, and then the total RNA was prepared according to the procedure attached to the kit. Further, the poly (A)⁺RNA was purified by means of oligo d(T) cellulose attached to the kit according to the procedure attached to the kit.

2) Construction of the cDNA Library

A double-stranded cDNA was synthesized using the above poly (A)⁺RNA of 5 μg as a material according to the procedure attached to a cDNA synthesis kit, Time Saver™ cDNA synthesis kit (manufactured by Pharmacia), and a BstXI adapter (manufactured by Invitrogen) was ligated thereto by means of a DNA ligation kit (manufactured by Takara Shuzo) according to the procedure attached to the kit. The removal of the free BstXI adapter was performed by means of the Size Sep 400 Spin Column attached to the kit according to the procedure attached to the kit to obtain about 100 μl of an adapter-ligated double-stranded cDNA.

And then, of about 100 μl of the thus prepared adapter-ligated double-stranded cDNA, 2 μl were used in one ligation reaction, and a cDNA library was constructed by ligating it with a PEF-BOS vector [Nuc. Acid Res., 18:5322 (1990)] treated in advance with a restriction enzyme BstXI and alkali phosphatase (manufactured by Takara Shuzo) by means of a cDNA ligation kit (manufactured by Takara Shuzo). The constructed cDNA library was transformed into the *Escherichia coli* cell line DH5 (manufactured by Toyobo) and was presumed to be an independent clone with the total size of about 2×10⁵. Fifty pools, each pool comprising 2,000 to 4,000 clones of transduced *Escherichia coli*, were prepared and then used in the following tests.

2. Cloning according to Direct Expression Method

1) Transfection into 293T Cells

The amplification of a cDNA was performed by culturing the above pooled *Escherichia coli* in the LB medium containing 50 μg/ml of ampicillin [Molecular Cloning: A Laboratory Manual, Sambrook et al., Cold Spring Harbor Laboratory Press (1989)], and a plasmid DNA was recovered from the *Escherichia coli* according to an alkaline method [Molecular Cloning: A Laboratory Manual, Sambrook et al., Cold Spring Harbor Laboratory Press (1989)]. The degree of the purification of the obtained plasmid DNA was enhanced by repeating ultra-centrifugation according to cesium chloride/ethidium bromide density-gradient centrifugation, and the purified plasmid DNA was transfected to a 293T cell [cell line prepared by transfecting an SV40 large T antigen cDNA into a 293 cell (Transformed primary embryonal kidney, human ATCC CRL 1573)] according to a calcium phosphate method.

Namely, 2 μg of the purified plasmid DNA was dissolved into 100 g 1 of a buffer solution containing 1 mM of Tris-HCl and 0.1 mM of EDTA, and after 14 μl of 2M CaCl₂ were added thereto, the resultant mixture was mixed with a buffer solution composed of 50 mM of HEPES (pH: 7.1), 280 mM of NaCl and 1.5 mM of sodium phosphate slowly, and then the obtained mixture was incubated at room temperature for 30 minutes and added to the 293T cells in 24-well plates. The 293T cells were cultured in the DMEM (manufactured by GIBCO) medium containing 10% fetal calf serum (FCS, manufactured by Bioproducts) under the conditions of 37° C. and 5% CO₂ for 2 days.

2) Analysis According to FACScan

The transduced 293T cells were removed from the 24-well plates in PBS containing 0.02% EDTA, and washed with an FACS buffer solution comprising PBS containing 2% FCS and 0.02% NaN₃ twice, and then suspended in 20 μl of the FACS buffer solution in the presence of 10 μg/ml of the above-mentioned monoclonal antibody RS38 as a primary antibody and incubated on ice for 20 minutes. After they were washed with the FACS buffer solution twice, they were further incubated on ice for 15 minutes, using an FITC-labeled anti-mouse Ig goat antibody (manufactured by Cappel) as a secondary antibody. Propidium iodide (PI) was added therein so that the final concentration of it became 1 μg/ml, and the mixture was further incubated on ice for 5 minutes, washed with the FACS buffer solution three times, and the cells were analyzed with light scattering measurement and viable cells alone were subjected to analysis by means of an FACScan (manufactured by Becton Dickinson).

3) Cloning of the cDNA Library

The plasmid DNAs recovered from *Escherichia coli* of 2,000 to 4,000 clones as one pool according to an alkaline method were transfected to 293T cells according to the above method, and the transfected cells were subjected to screening according to the above FACS analysis. A peak strongly stained with the mouse monoclonal antibody RS38 was recognized in the 25th pool of the 293T cells. The plasmid DNA was transduced into *Escherichia coli* DH5 (manufactured by GIBCO BRL) again, and it was inoculated onto an LB agar plate containing 50 μg/ml of ampicillin.

About 2,000 clones forming colonies were inoculated one by one onto an agar plate with its bottom divided into a net-like state so that the position of a clone inoculated was recognized at a rate of 100 clones per plate, and two series of each plate were prepared. 20 pools, each pool comprising 100 clones, were prepared in the same way, and *Escherichia coli* was cultured in the LB medium containing 50 μg/ml of ampicillin. After plasmid DNAs were recovered according to an alkaline method, they were transfected to 293T cells according to a calcium phosphate method, and the transfected cells were subjected to FACScan analysis in the same manner as above. As a result of the FACScan analysis, 100 clones of *Escherichia coli* were isolated one by one from one pool recognized to be positive, and each clone was cultured, and then plasmid DNAs were recovered according to an alkaline method. Each plasmid DNA was transfected to 293T cells according to a calcium phosphate method, and FACScan analysis was performed in the same manner as above to obtain a single positive clone, which was designated as pRS38-BOS.

The clone was subjected to a sequence reaction using an Auto Read sequencing kit (manufactured by Pharmacia) and an Auto Cycle sequencing kit (manufactured by Pharmacia) according to the procedure attached to the kits, and the determination of its DNA sequence was performed by means of an A. L. F.™ DNA sequenator (manufactured by Pharmacia). As a result, it was a gene with the full length of 996 bp (sequence No. 2 of the sequence table) to be presumed to encode a sequence of the 180 amino acid residues from the longest open reading frame, and as a result of performing homology retrieval according to data bases SWISS PLOT and NBRL using a gene analysis software Genetex, it was recognized to be a novel gene.

4) Investigation of Expression According to Northern Blotting Analysis

Preparation of poly (A)+RNA from the synovial cell line SynSV6-14 derived from patients with RA, the bone marrow stromal cell line RASV5-5 derived from patients with RA and the bone marrow stromal cell line NFSV1-1 derived from healthy donors was performed by using a Fast Track™ mRNA isolation kit version 3.2 (manufactured by Invitrogen) to perform northern blotting analysis (Molecular Cloning; A Laboratory Manual, Sambrook et al., Cold Spring Habor Laboratory Press, 1989). That is, cell lines cultured in ten 10-centimeter culture dishes were recovered and homogenized, and then the total RNA was prepared according to the procedure attached to the kit. Further, the poly (A)+RNA was purified by means of oligo d(T) cellulose attached to the kit according to the procedure attached to the kit.

Figure 1:
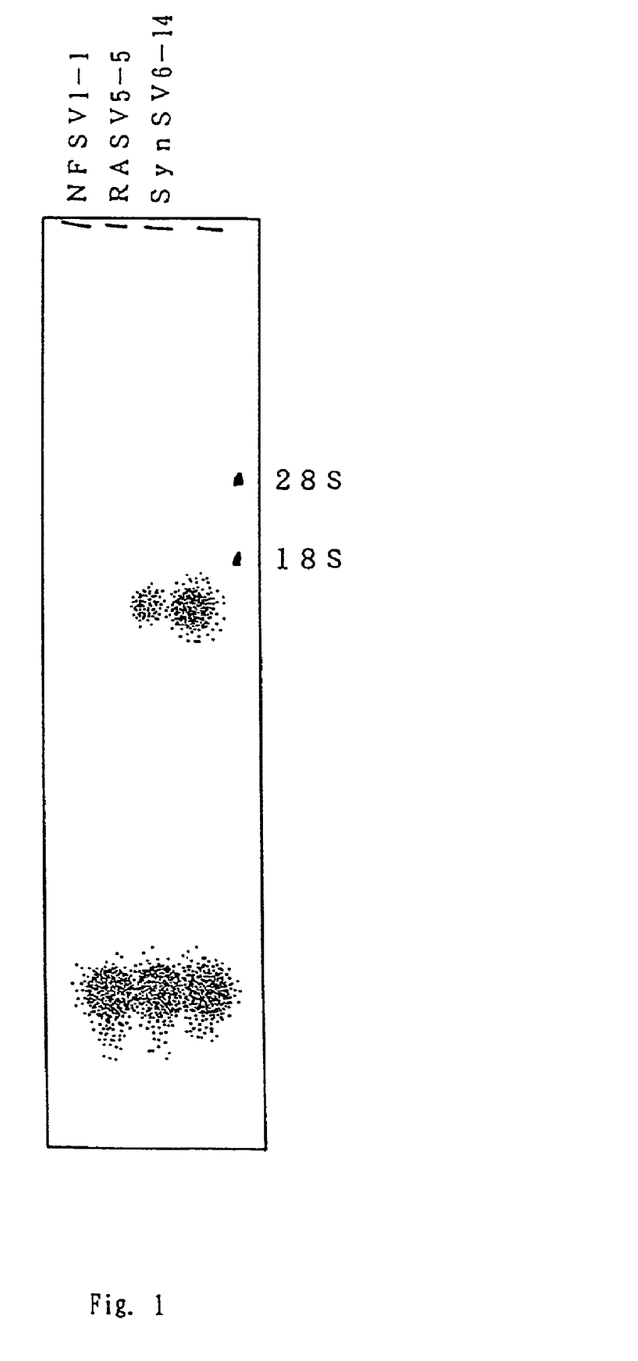
FIG. 1 shows the results (photograph according to agarose gel electrophoresis) of analyzing a gene obtained in Examples of the present invention according to northern blotting analysis.

Labelling a probe was performed by using a Multiprime DNA labelling system (manufactured by Amersham). That is, a 315bp fragment was prepared by digesting an insert believed to encode RS38 inserted into the BstXI site of pEF-BOS with a restriction enzyme HindIII and then a labelled probe was prepared according to the procedure attached to the kit. The poly (A)+RNA prepared from SynSV6-14, RASV5-5 and NFSV1-1, 3 µg per lane, was subjected to agarose gel electrophoresis, and then blotting was performed according to a capillary method by using a Gene Screen Plus™ (manufactured by Du Pont) as a hybridization transfer membrane. Hybridization was performed at 65° C. overnight by using a Gilbert & Church buffer comprising 0.5 M $NaPO_4$, 1mM EDTA, 7% SDS and 1% BSA, pH 7.0. After the completion of hybridization, the membrane was washed with 2×SSC at room temperature four times and further with 0.1×SSC and 0.1% SDS at 55° C. twice, and then placed face to face with an X-ray film to perform autoradiography overnight. As a result, an apparent band of about 1.0 kb was detected on SynSV6-14 as shown in FIG. 1.

3. Expression by a BALB3T3 Cell

The novel molecule was transfected into a BALB3T3 cell and the expression in mammalian cells was examined.

Namely, 20 µg of pRS38-BOS and 2 µg of pSv2neo which has a neomycin-resistant gene [P. J. Souethem and P. Berg, J. Mol. Appl. Genet., 1:327 (1982)] were added into 0.8 ml of aliquot of 1×10$^7$ cells/ml, and incubated on ice for 10 minutes, and then subjected to transfection by means of a Gene Pulser (manufactured by BioLad) under the conditions of 250 V and an electrostatic volume of 250 µF to accomplish transduction simultaneously.

Further, after it was incubated on ice for 10 minutes, the cell was suspended in the DMEM medium (manufactured by GIBCO) containing 2 mg/ml of G418 and 10% FCS (manufactured by Bioproducts) and cultured in 24-well plates. The replacement of a culture medium was performed every three days, and about 2 weeks later, transformed cell lines BALB3T3 38-1, 38-3 and 38-9 responding to the above mouse monoclonal antibody RS38 were obtained from the well forming a single colony of well-grown adhesion cells having neomycin resistance. In addition, as a control cell was obtained a transformed cell line BALB3T3 38-4 not responding to RS38 but having neomycin resistance.

4. Biological Properties of the Novel Molecule

1) Growth-Supporting of Mouse Pre-B Cell Lines

The biological properties of the novel molecule were analyzed using a mouse pre-B cell line DW34 growing dependent on stromal cells with the number of grown cells as an index according to the following method.

Figure 2:
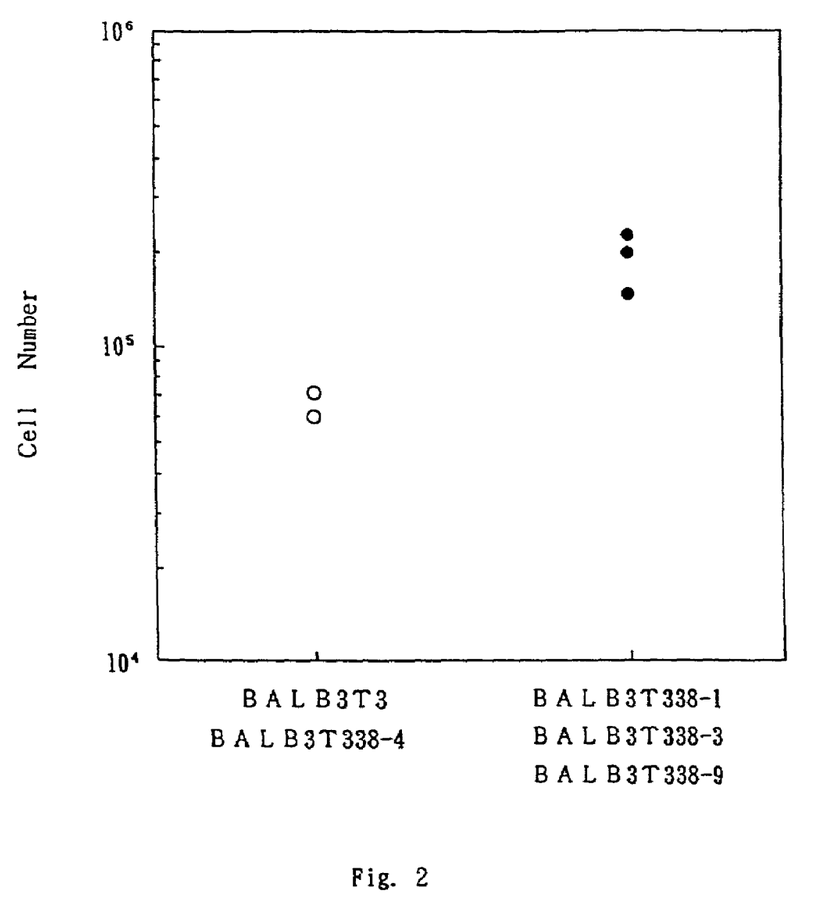
FIG. 2 shows the growth ability of the mouse pre-B cell line DW34 of a membrane protein obtained in Examples of the present invention.

First of all, transduced cell lines BALB3T3 38-1, 38-3 and 38-9 and control cell lines BALB3T3 and BALB3T3 38-4 were cultured in 24-well plates until they became subconfluent, radiation of 30 Gy was irradiated thereupon, DW34 of 2×10$^3$ per well was added therein, and the resultant product was cultured in the RPMI-1640 (manufactured by GIBCO) medium containing 10% FCS (manufactured by Bioproducts) under the conditions of 37° C. and 5% $CO_2$ for 4 days. The number of viable cells of DW34 in each well was counted with trypan blue dye exclusion to analyze a growth-supporting ability. As a result, the growth of DW34 was enhanced in the transduced cell lines BALB3T3 38-1, 38-3 and 38-9 in comparison with control cell lines BALB3T3 and BALB3T3 38-4 as shown in FIG. 2.

5. Physicochemical Properties of the Novel Molecule

1) Analysis of the N Terminal

The analysis of the hydrophobic region and the hydrophilic region of the gene obtained as above was performed by using a DNA analysis software Gene Works. The results of the analysis are shown in FIG. 3. As a result, the region of 28 amino acid residues from the 21st Lys to the 48th Ala shown in sequence No. 1 of the sequence table had the highest hydrophobic properties, and therefore it was presumed to be type of a protein to pass through the cell membrane, having a domain passing through cell membrane and an intracellular domain at the side of the N terminal of mature protein.

INDUSTRIAL APPLICABILITY

As described in detail above, the present invention relates to a gene encoding a novel membrane protein polypeptide having pre-B cell growth-supporting ability, a vector containing said gene, transformants transformed by said vector, and a method for producing a novel membrane protein having pre-B cell growth-supporting ability using said gene, and therefore the gene of the present invention is capable of encoding the membrane protein on the synovial cell derived from patients with rheumatoid arthritis (RA).

The homogeneous and purified novel membrane protein polypeptide can be produced in large quantities by inserting the gene of the present invention into a suitable vector and then transforming ordinary host cells, and in addition, monoclonal antibodies recognizing said membrane protein polypeptide can be produced by using the synovial cell derived from patients with rheumatoid arthritis (RA) as an antigen for immunization. Thus, according to the present invention, it becomes possible to identify rheumatoid arthritis (RA) and also prepare reagents for the clinical diagnosis thereof.

What is claimed is:

1. An isolated antibody which has a positive reactivity against cell lines U937 and K562 and which recognizes a polypeptide consisting of the amino acid sequence shown in SEQ ID NO: 1, said polypeptide having pre-B cell growth-supporting ability.

2. The antibody of claim 1 which is a monoclonal antibody.

3. The monoclonal antibody of claim 2 which is IgM.

4. The antibody of claim 2 which is produced by the hybridoma deposited under the accession number FERM BP-4433.

5. A hybridoma which produces a monoclonal antibody which has a positive reactivity against cell lines U937 and K562 and which recognizes a polypeptide consisting of the amino acid sequence shown in SEQ ID NO: 1, said polypeptide having pre-B cell growth-supporting ability.

6. The hybridoma of claim 5, which produces an IgM monoclonal antibody.

7. The hybridoma of claim 5, deposited under accession number FERM BP-4433.

* * * * *